United States Patent
Krutikov et al.

(10) Patent No.: US 6,730,787 B1
(45) Date of Patent: May 4, 2004

(54) 2,4DIOXO-5-ARYLIDENIMINO-1,3-PYRIMIDINES

(75) Inventors: Viktor I. Krutikov, St. Peterburg (RU); Rimma I. Ashkinazi, St. Peterburg (RU)

(73) Assignee: Viromax, LLC, Fort Lee, NJ (US)

( * ) Notice: Subject to any disclaimer, the term of this patent is extended or adjusted under 35 U.S.C. 154(b) by 0 days.

(21) Appl. No.: 09/869,792

(22) PCT Filed: Dec. 4, 1998

(86) PCT No.: PCT/RU98/00407

§ 371 (c)(1),
(2), (4) Date: Jul. 2, 2001

(87) PCT Pub. No.: WO00/34250

PCT Pub. Date: Jun. 15, 2000

(51) Int. Cl.[7] .......................................... C07D 239/545
(52) U.S. Cl. ....................................................... 544/311
(58) Field of Search ......................................... 544/311

(56) References Cited

PUBLICATIONS

Chemical Abstracts vol. 79: 532 55 (1973) Chakraber.*
Chemical Abstracts, vol. 124: 145 723 (1996) Kuzmenko et al.*
Chemical Abstracts, vol. 114:164148 (1991) Hurst et al.*
Chemical Abstracts, vol. 114:74161 (1991) Cherayath et al.*
Chemical Abstracts, vol. 127:293188 (1997) Seitembov.*
Chemical Abstracts, vol. 86:89762 (1977) Yoheda et al.*

* cited by examiner

Primary Examiner—John M. Ford
(74) Attorney, Agent, or Firm—I. Zborovsky

(57) ABSTRACT

The invention relates to medicine, and more specifically to pharmacology, and in particular to synthetic biologically active derivatives of pyrimidine, and it is designated mainly for use as antiviral, immune-stimulating, antichlamydial, antituberculous, psychodepressant, analgesic, and hepatoprotective remedies. Besides that, these compounds may be used for treating malignant neoplasms, and also in veterinary. The objective of the invention is obtaining new chemical substances possessing pronounced biological activity of wide range. The proposed objective is achieved by synthesis of 2,4-dioxo-5-arylidenimino-1,3-pyrimidines of the general formula

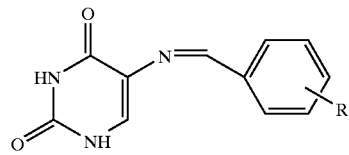

where R is chosen out of group H, OH, alkoxyl, dialkylamino, benzo, dibenzo, or 3,4-dioxolano General method of producing the claimed compounds and example of synthesis, a list of 25 compounds synthesized and tested, results of identification, and data on wide comparative testing their biological properties and toxicity are presented.

20 Claims, No Drawings

2,4 DIOXO-5-ARYLIDENIMINO-1,3-PYRIMIDINES

CROSS-REFERENCE TO A RELATED APPLICATION

This is a 371 or PCT/RU 98/00407, filed Dec. 1, 1998.

FIELD OF THE INVENTION

The invention relates to medicine, and more specifically to pharmacology, and in particular to synthetic biologically active derivatives of pyrimidine.

The claimed compounds possess pronounced antiviral, immune-stimulating (interferon-inducing), antichiamydial, antituberculous, psychodepressant, analgesic, and hepato-protective activities.

Compounds are mainly intended for use in medicine practice for treating viral infections, the infections caused by chlamydia, the diseases followed by immune-deficiency, in particular, malignant neoplasms, and also tuberculosis. Besides that, the given compounds can be used in veterinary for the same purposes.

TECHNICAL LEVEL

It is known that microbial and viral diseases are one of the most significant problems of modern medicine. Most of them hardly respond to treatment. It is connected with lack of efficiency of current drugs as well as high rate of variability of microorganisms that leads to origination of resistant forms [1, 2, 8].

Viral diseases often take a course on the background of lowering activity of the immune system, and they are followed by secondary infections; the same is also true for oncologic diseases. Therefore the problem of the development of effective antiviral or antitumoral drugs is closely related with the searching for remedies intended for treating the immune-deficient states of various origination.

Existing antiviral drugs may be conventionally divided into two groups according to types of mechanisms of their action. An action of the drugs of the first group involves suppression of virus reproduction in a body [1]. Antiviral drugs of the second group produce their effect though stimulating the body's immune protection and increase of producing endogenic interferons [2] to a greater extent rather than affecting the viruses in themselves. Interferons and their inducers are also used for treatment of a various tumoral diseases [3].

The given invention falls into the second group.

R-aminouracils of the following general formula:

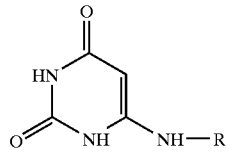

where R=phenyl, 2-methylphenyl, 3-methylphenyl, 4-methylphenyl, 4-bromophenyl, 2,4-dimethylphenyl, 2,5-dimethylphenyl, 2,6-dimethylphenyl, 2-chlorophenyl, 2-chlorophenyl, 3-chlorophenyl, 1-naphthyl, 2-naphthyl, cyclohexyl, may be chemical analogs of the claimed compounds. These analogs are described, for example, in [9].

The closest, by its chemical nature, to the claimed compounds is 6-[[3-[4-(2-methoxyphenyl)-1-piperazinyl]propyl]-amino]-1,3-dimethyluracil, which was taken by us as the prototype.

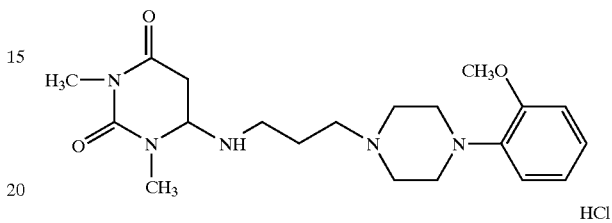

6-[[3-[4-(2-methoxyphenyl)- 1-piperazinyl]propyl]-amino]-1,3-dimethyluracil produces an hypotensive action. Its major application is to decrease the arterial pressure under hypertensive crisis. It is described in details in [10].

Unfortunately, range of its biological activity is comparatively narrow.

OBJECTIVE OF THE INVENTION

An objective of the invention is obtaining new chemical compounds possessing a wider range of biological activity, including antiviral activity (with respect to Herpes Simplex virus), immune-stimulating activity (at the expense of induction of producing endogenic interferons in a body), and antimicrobial activity. In other words, the objective of the invention is to provide chemical synthesis of biologically active compounds that outperform the prototype in their biological activity, and also in the range of action.

SUBJECT OF THE INVENTION

The proposed objective is achieved by synthesis of new chemical compounds, that are 2,4-dioxo-5-arylidenimino-1, 3-pyrimidines of the general formula (1)

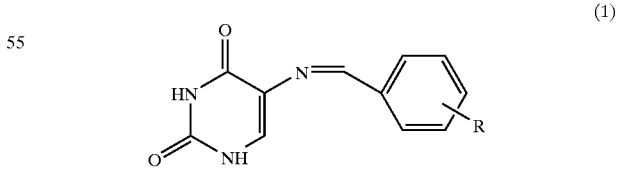

(1)

where R is taken from the group of H, OH, alkoxyl, dialkylamino, benzo, dibenzo, or 3,4-dioxolano A list of all 25 synthesized and identified compounds is presented in Table 1.

TABLE 1

List of the synthesized compounds that are claimed.

| | Number and name of the compound | R | Empirical formula |
|---|---|---|---|
| I- | 2,4-dioxo-5-benzylidenimino-1,3-pyrimidine | H | $C_{11}H_9N_3O_2$ |
| II- | 2,4-dioxo-5-(4-chlorobenzylidene) imino-1,3-pyrimidine | 4-Cl | $C_{11}H_8N_3O_2Cl$ |
| III- | 2,4-dioxo-5-(3-chlorobenzylidene) imino-1,3-pyrimidine | 3-Cl | $C_{11}H_8N_3O_2Cl$ |
| IV- | 2,4-dioxo-5-(2-chlorobenzylidene) imino-1,3-pyrimidine | 2-Cl | $C_{11}H_8N_3O_2Cl$ |
| V- | 2,4-dioxo-5-(4-bromobenzylidene) imino-1,3-pyrimidine | 4-Br | $C_{11}H_8N_3O_2Br$ |
| VI- | 2,4-dioxo-5-(4-hydroxybenzylidene) imino-1,3-pyrimidine | 4-OH | $C_{11}H_9N_3O_3$ |
| VII- | 2,4-dioxo-5-(2,4-dihydroxybenzylidene) imino-1,3-pyrimidine | 2,4-$(OH)_2$ | $C_{11}H_9N_3O_3$ |
| VIII- | 2,4-dioxo-5-(2-hydroxy-5-bromobenzylidene) imino-1,3-pyrimidine | 2-OH-5-Br | $C_{11}H_8N_3O_3Br$ |
| IX- | 2,4-dioxo-5-(2-hydroxy-5-chlorobenzylidene) imino-1,3-pyrimidine | 2-OH-5-Cl | $C_{11}H_8N_3O_3Cl$ |
| X- | 2,4-dioxo-5-(4-fluorobenzylidene) imino-1,3-pyrimidine | 4-F | $C_{11}H_8FN_3O_2$ |
| XI- | 2,4-dioxo-5-(2,4-dichlorobenzylidene) imino-1,3-pyrimidine | 2,4-$Cl_2$ | $C_{11}H_7N_3O_2Cl_2$ |
| XII- | 2,4-dioxo-5-(2-hydroxy-3,5-dichlorobenzylidene) imino-1,3-pyrimidine | 2-OH-3,5-$Cl_2$ | $C_{11}H_7N_3O_3Cl_2$ |
| XIII- | 2,4-dioxo-5-(2-hydroxy-3,5-dibromobenzylidene) imino-1,3-pyrimidine | 2-OH-3,5-$Br_2$ | $C_{11}H_7N_3O_3Br_2$ |
| XIV- | 2,4-dioxo-5-(4-methoxybenzylidene) imino-1,3-pyrimidine | 4-$OCH_3$ | $C_{12}H_{11}N_3O_3$ |
| XV- | 2,4-dioxo-5-(4-hydroxy-3-methoxybenzylidene) imino-1,3-pyrimidine | 4-OH-3-$OCH_3$ | $C_{12}H_{11}N_3O_4$ |
| XVI- | 2,4-dioxo-5-(4-nitrobenzylidene) imino-1,3-pyrimidine | 4-$NO_2$ | $C_{11}H_8N_4O_4$ |
| XVII- | 2,4-dioxo-5-(3-nitrobenzylidene) imino-1,3-pyrimidine | 3-$NO_2$ | $C_{11}H_8N_4O_4$ |
| XVIII- | 2,4-dioxo-5-(2-nitrobenzylidene) imino-1,3-pyrimidine | 2-$NO_2$ | $C_{11}H_8N_4O_4$ |
| XIX- | 2,4-dioxo-5-(2-hydroxy-5-nitrobenzylidene) imino-1,3-pyrimidine | 2-OH-5-$NO_2$ | $C_{11}H_8N_4O_5$ |
| XX- | 2,4-dioxo-5-(2-hydroxy-5,6-benzobenzylidene) imino-1,3-pyrimidine | 2-OH-5,6-benzo | $C_{15}H_{11}N_3O_3$ |
| XXI- | 2,4-dioxo-5-(3,4-dioxolano-benzylidene) imino-1,3-pyrimidine | dioxolan-3,4-diyl | $C_{12}H_9N_3O_4$ |
| XXII- | 2,4-dioxo-5-(2-nitro-5,6-dioxolano-benzylidene) imino-1,3-pyrimidine | 2-$NO_2$-dioxolan-4,5-diyl | $C_{12}H_8N_4O_6$ |
| XXIII- | 2,4-dioxo-5-(2,3,5,6-dibenzobenzylidene) imino-1,3-pyrimidine | 2,3,5,6-dibenzo | $C_{19}H_{13}N_3O_2$ |
| XXIV- | 2,4-dioxo-5-(2-hydroxy-3,5-diiodobenzylidene) imino-1,3-pyrimidine | 2-OH-3,5-$I_2$ | $C_{11}H_7I_2N_3O_3$ |
| XXV- | 2,4-dioxo-5-(4-dimethylamino-benzylidene) imino-1,3-pyrimidine | 4-$N(CH_3)_2$ | $C_{13}H_{14}N_4O_2$ |

The compounds claimed are new because they are not known from available information sources.

The presence of effective biological activity of wide range that the claimed compounds possess does not obviously stem from preceded level of technique, i.e. the presence of the indicated activities is not obvious for a specialist.

DISCLOSURE OF THE INVENTION

The subject matter of the present invention is explained below by:
The method of producing all 25 claimed compounds I–XXV
Example of synthesizing 2,4-dioxo-5-(2-hydroxy-3,5-dichlorobenzylidene)imino-1,3-pyrimidine
Data on PMR spectroscopic study of compounds I–XXV (Table 2)
Data on experiments for determining the biological activity of the claimed compounds as compared with known modern effective remedies of the same designation; that experiments are:
Experiment 1. Determination of effect of the claimed compounds on Herpes Simplex virus (with Table 3).
Experiment 2. Determination of interferon-inducing activity of the claimed compounds (with Table 4).
Experiment 3. Determination of effect of the claimed compounds on *Chlamydia trachomatis* (with Table 5).
Experiment 4. Determination of antimicrobial effect of the claimed compounds (with Table 6).
Experiment 5. Determination of antidepressant action of the claimed compounds (with Table 7).
Experiment 6. Determination of analgesic action of the claimed compounds (with Table 8).
Experiment 7. Determination of hepatoprotective activity of the claimed compounds (with Table 9).
Experiment 8. Determination of the maximal tolerant dose of the claimed compounds (with Table 10).

Method of Producing Compounds I–XXV

Target 2,4-dioxo-5-aryledenimino-1,3-pyrimidines are obtained through interaction between 5-aminouracil and the corresponding aldehydes (see R). The mixture ethanol-water 1:1 is used as a solvent. While boiling mixture of aldehyde and aminouracil, colorless crystalline precipitation is deposited. Output of products is about 45–95% as compared to the theoretical output.

Example of synthesizing 2,4-dioxo-5-(2-hydroxy-3,5-dichlorobenzylidene)imino-1,3-pyrimidine 1.27 g of 5-aminouracil and 150 ml of water are placed into a tube. The mixture is heated while mixing until residue dissolves completely. In parallel, 1.91 g of 3,5-dichlorosalicylic aldehyde are dissolved in 50 ml of ethanol and add to the solution of 5-aminouracil. Brightly orange residue is deposited at once. The reaction mixture is boiled when stirring for 1 hour, and then the stirring is continued for 1 hour at the room temperature. Then the reaction mixture is left for a night. The deposited precipitation is filtered, washed with warm water, alcohol, and dried. The obtained output is 92%.

The other claimed compounds are synthesized analogously, using other R. A notable difference concerns only output of the target product.

The compounds of the general formula are colorless or brightly colored crystalline substances, soluble in dimethyl-sulfoxide, pyridine. Melting points of all the substances are above 300° C.

Individuality of the compounds is proved by thin-layer chromatography on the plates Silufol UV-254; the elutriator was carbon tetrachloride—isopropanol in the ratio 9:1. The structure of the synthesized compounds is proved by the PMR spectroscopic method.

TABLE 2

Results of PMR spectroscopic study of the compounds I-XXV

| N of compound | CH=N | NH | CH(Ur) |
|---|---|---|---|
| I | 9.5 | 11.5 | 8.0 |
| II | 9.4 | 11.1 | 7.8 |
| III | 9.7 | 11.3 | 7.7 |
| IV | 9.5 | 11.2 | 8.1 |
| V | 9.6 | 11.3 | 7.9 |
| VI | 9.5 | 11.4 | 8.1 |
| VII | 9.7 | 11.5 | 7.9 |
| VIII | 9.4 | 11.4 | 8.1 |
| IX | 9.5 | 11.5 | 7.9 |
| X | 9.6 | 11.4 | 7.2 |
| XI | 9.6 | 11.3 | 8.0 |
| XII | 9.5 | 11.2 | 7.9 |
| XIII | 9.7 | 11.5 | 7.8 |
| XIV | 9.5 | 11.1 | 8.1 |
| XV | 9.7 | 11.3 | 7.9 |
| XVI | 9.4 | 11.2 | 7.8 |
| XVII | 9.7 | 11.2 | 7.9 |
| XVIII | 9.6 | 11.2 | 8.1 |
| XIX | 9.5 | 11.3 | 8.0 |
| XX | 9.3 | 11.4 | 8.0 |
| XXI | 9.7 | 11.5 | 8.2 |
| XXII | 9.5 | 11.5 | 8.1 |
| XXIII | 9.7 | 11.3 | 7.9 |
| XXIV | 9.5 | 11.5 | 7.8 |
| XXXV | 9,6 | 11,4 | 8,0 |

Confluent signal from two protons of imino groups of the uracil circle is characteristic for PMR-spectra (Table 2 presents an average value of the chemical shift).

Data on Experimental Determining the Biological Activity of the Claimed Compounds Experiment 1. Determination of Effect of the Claimed Compounds on Herpes Simplex Virus.

An antiviral activity was determined with respect to Herpes Simplex virus of the type I (HSV-I/Leningrad/248/88) using commonly accepted method [5]. Viruses were grown on a continuous culture of Vero cells that have been received from the Bank of Cell Cultures of the Institute of Cytology of the Russian Academy of Science.

Procedure of an Experiment.

A virus in a final concentration of $10^2$ $TID_{50}$/ml (TID is a tissue infection dose) and the claimed compounds, dissolved in DMSO in final concentrations of 100, 10 and 1 mg/l, were added to cells that were grown on the RPMI-1640 medium containing 10% of fetal calf serum and placed into wells of the 96-well plate. 5 separate wells were used for each of tested concentrations of an agent. The plate was incubated for 60 minutes at 37° C. in a $CO_2$-incubator. After the incubation, the virus was removed and then a fresh medium containing claimed compounds in used concentrations was again introduced. Results were evaluated basing on presence of cytopathogenic effect on the cells after 36 hours of incubation at 37° C. in the $CO_2$-incubator.

The next controls were used in the experiment:
1. Control of cell culture (capability to grow properly)
2. Control of the virus (assessment of capability for reproduction)
3. Control of an antiviral activity of an antiviral drug Acyclovir
4. Control of compounds (toxicity of compounds)
5. Control of a solvent (DMSO) as to toxicity.

To estimate a cytopathic effect of the virus, a quantity of the unchanged cells was calculated in 100 visual fields formed by a special net of an eyepiece-micrometer of an inverted microscope. The data obtained are shown in Table 3.

TABLE 3

Effect of the claimed compounds on the Herpes Simplex virus at the compound concentration of 100 μg/ml

| Compound | Quantity of the unchanged cells (% of protection) |
|---|---|
| Cell control | 10000* |
| Acyclovir (30 μg/ml) | 8000* (80%) |
| DMSO | 10000 |
| XII | 9000 (90%) |
| XIII | 8000 (80%) |
| XIX | 8000 (80%) |

*number of cells in 100 visual fields under consideration

The obtained results show that the claimed compounds presented in Table 3 possess antiherpetic activity which is comparable with that of a standard drug Acyclovir. The remainder of the claimed compounds demonstrated the less marked activity in suppressing reproduction of Herpes virus in the adopted experimental conditions.

Experiment 2. Determination of Interferon-inducing Activity of the Claimed Compounds Interferon synthesis induction caused by the claimed compounds was conducted on a primary culture of human lymphocytes (these cells in a human organism are the main producers of λ-interferon). To obtain lymphocyte culture, fresh blood (within 12 hours after sampling) from healthy donors (not of group II) was used. To separate lymphocytes, heparinized blood obtained from healthy donor was centrifuged in a density gradient ficoll-verografin of 1.71 g/cm³ in order to extract a fraction of immunocompetent cells. This fraction was selected and diluted with the nutrient medium RPMI-1640, containing 5% of fetal calf serum, 0.3 mg/ml of L-glutamin, 100 un/ml of penicillin, and 50 µg/ml of streptomycin. The concentration of lymphocytes was considered after dying them with methylene blue and calculation of cell number in a chamber of a hemocytometer. Initial solutions of the claimed compounds were diluted with the nutrient medium RPMI-1640 so that the final concentrations of the compounds which were obtained after introduction of lymphocyte suspension, constituted the raw: 100 µg/ml, 10 µg/ml, 1 µg/ml. The final concentration of lymphocytes in the induction mixture was $3 \times 10^6$ cell/ml.

In parallels to the test samples the following controls were done:

1) Control of spontaneous production of interferons (IFN) by lymphocytes.
2) Control of the process course under the action of the standardized IFN inductor N-methyl-N-(α,D-glucopyranosyl)ammonium- 10-methylenecarboxylate acridone (Cyclopherone).
3) Control of the process course under the action of the standardized IFN inductor Neovir (sodium 10-methylenecarboxylate-9-acridone) with corresponding content of DMSO in experimental samples.
4) Control of spontaneous production of interferon in presence of DMSO taken in an amount corresponding to the test samples.

Control and test samples were incubated for 24 hours at the temperature of 37° C. After incubation, the samples were centrifuged at 2,000 G to deposit cell elements, and IFN-containing supernatant was separate out of the samples; then the supernatant was analyzed for the quantitative content of IFN. Cell deposition was resuspended in the preceding volume of nutrient medium, colored with vital dye trypan blue, and cell number was counted in a chamber of a hemocytometer (as described above) to determine cytotoxic effect of the compounds.

Quantitative determination of the content of IFN in control and test samples was conducted using the immunoenzyme test system Pro Con IF2 Plus, that is intended for determination of IFN-α, which is produced by TOO <<Protein contour>>. The solid-phase immunoenzyme method, utilizing horse radish peroxidase as an indicator enzyme, was used to determine the quantity of interferon in the samples. Activity of the bonded peroxidase was measured using an automatic photometer for microplates with a microprocessor at the wavelength of 450 nm.

To calculate the results, the activity of IFN in standard IFN solutions containing known quantities of preparation was determined in parallel. Based on the obtained results, a calibrating curve was formed, which allows to obtain data expressed in international units (IU) of activity, using the microprocessor of the automatic photometer. The results of the analysis are expressed in IU of activity of IFN per ml in the given induction system, which contains $3 \times 10^6$ lymphocyte/ml. Each test and control point was investigated in four parallels.

Controls of immunoenzyme reaction:

1. Control of DMSO with a nutrient medium.
2. Control of system components (according to an instruction). All results were considered only if controls complied with passport data of the system.

The obtained data were undergone a statistical analysis using t-criterion, and calculation of the confident interval of probability at p=0.05 was carried out. Coincidence between the results obtained in the parallel tests was analyzed.

The investigations performed resulted in the fact, that, among the claimed substances, there are samples possessing capability to induce synthesis of IFN (Table 4).

TABLE 4

Quantitative evaluation of IFN-inducing activity of the claimed compounds

| | | Content of IFN in induction mixture after 24-hour incubation at various concentrations (µg/ml) of substances, IU/3 × $10^4$ lymph./ml | | |
|---|---|---|---|---|
| N | Substance | 100 mg/l | 10 mg/l | 1 mg/l |
| 1. | Control of lymphocytes | 0 | 0 | 0 |
| 2. | Cycloferon | 75 ± 2 | 35 ± 1 | 7,8 ± 1,2 |
| 3. | Neovir | 83,2 ± 1.6 | 39,0 ± 1,3 | 13,1 ± 0,8 |
| 4. | Poly I/poly C | —* | 48.6 ± 2.0 | 13.5 ± 1.4 |
| 5. | DMSO | 0 | 0 | 0 |
| 6. | IV | 123,6 ± 0,5 | 62,5 ± 1,3 | 15,2 ± 0,3 |
| 7. | XV | 105 ± 2 | 54,2 ± 1,8 | 4,5 ± 1,6 |

*compound of this concentration was not tested

The other claimed compounds demonstrated lower interferon-inducing activity.

Experiment 3. Determination of Effect of the Claimed Compounds on *Chlamydia trachomatis*.

The antichiamydial activity of the claimed compounds was studied in respect to *C.trachomatis* D323, which is a standard strain contained in the collection of the department of microbiology of St. Petersburg State Pavlov Medical University. This strain was derived from a patient having chlamydial urethritis; the strain has a morphology and physiological activity that are characteristic for representatives of this type; the strain is sensitive to action of compounds that are used to treat chlamydial infection. Cell cultures McCoy and L929 obtained from the Institute of Cytology of RAS were used in this work.

Procedure of an Experiment.

Cells were grown in flasks made of neutral glass in the medium RPMI-1640 containing 10% of fetal calf serum. The test was performed in flat-bottom flasks made of glass (non-toxic), that were supplied with cover glasses. The cells were introduced into the medium in the final concentration of $1 \times 10^6$ cell/ml. After a monolayer had been obtained, standard infectious dosages of chlamydia, which had been stored in a frozen state at the temperature of −70° C., were introduced into test tubes. Simultaneously, tested compounds in a final concentration of 100 mg/l were added to the cells. The sample was centrifuged at 2400 G for 60 minutes at a room temperature and incubated at 37° C. for 2 hours. After this, the nutrient medium was replaced with a new medium, containing 5% of fetal calf serum and cycloheximide (2 µg/ml), with repeated introduction of the claimed compounds in the preceding concentration. The samples were doubled using the medium without cycloheximide so as to exclude its effect on the investigated compounds. The samples were incubated for 48 hours in $CO_2$-incubator.

The controls included:

1. Control of cell culture
2. Control of effect of solvents
3. Control of effect of chlamydia in absence of any compounds
4. Control of sensitivity of chlamydia to standard antimicrobial compound Ciprofloxacin
5. Control of the tested compounds as to toxicity in respect to the cell culture.

Evaluation of the results was carried out by the way of determination of Chlamydial cytoplasmatic inclusions (CPI) that was conducted by the method of immunofluorescence (MicroTrack *Chlamydia trachomatis* Direct Specimen Test), and by the way of determination of antigens of chlamydia that was conducted by means of CylaMonoScreen (Russian-British Joint Venture 66 Regent's Parc Road London NWI 7SX) [6, 7]. The effect of the compound was determined by analysis of the monolayer state and number of cells with CPI when compared with the control (cell culture infected with C.trachomatis D323); in doing so, the number of unchanged cells, that were counted in 100 visual fields obtained using the eyepiece-micrometer, was taken into consideration.

Results of the control samples satisfying to the requirements of the experiment, are the following:

control of cell culture: morphology of cells and state of monolayer correspond to the given type of the cells;

control of chlamydia growth in the cell culture: presence of CPI in the monolayer;

control of effect of standard antimicrobial agent: reduction of number of CPI in the monolayer as compared to the preceding control;

control of toxicity of the claimed compounds: toxicity is absent;

control of effect of solvents: toxic effect on cells is absent.

The results of performed tests are presented in Table 5.

TABLE 5

Effect of the claimed substances on C. trachomatis

| NN | Substance | Number of unchanged cells |
| --- | --- | --- |
| 1. | Cell control | 8.000 (100%) |
| 2. | DMSO | 8.000 (100%) |
| 3. | Control of infected cells | 6.000 |
| 4. | Ciprofloxacin (100)* | 7.000 (50%)** |
| 5. | XI | 7.700 (55%) |
| 6. | XXV | 7.700 (55%) |

*concentration of the drug, mg/l
**percentage of cell protection from infection is given in brackets.

The data obtained give an evidence of the fact that the claimed compounds XI and XXV, shown in Table 5, are of marked activity against chlamydia, and this activity is superior to the activity of the standard drug Ciprofloxacin.

The other claimed compounds possess less marked activity as to protection of cells from chlamydia in the adopted conditions of experiment.

Experiment 4. Determination of Antimicrobial Effect of the Compounds

To determine an antimicrobial activity a standard strain—Mycobaciterium tuberculosis H37RV, which is sensitive to all the antimicrobial agents, was used. Antimycobacterial effect was estimated by the serial dilution method.

Substances were dissolved in dimethyl-sulfoxide (DMSO) and titrated in the medium N-1, so that the preparation was contained in separate test tubes with the medium in concentrations from 200 to 0.025 mg/l. The concentrations of the substance in the medium in adjacent test tubes differed by the factor of two. DMSO titrated in the same way as the substance was utilized for the control. The result was considered after a 72-hour cultivation of the bacteria at 37° C.

M.tuberculosis H37Rv were grown on the Soton medium which contained 10% of horse serum, and the density of microbial suspension when seeding was $50 \times 10^6$ cell/ml.

Standart tuberculostatic compounds were utilized as the controls. The results obtained for the used strain are summarized in Table 6.

TABLE 6

Minimal inhibitory concentration (MIC) regarding M tuberculosis H37R (mg/l)

| Compound | MIC, mg/l |
| --- | --- |
| VIII | 100 |
| XII | 100 |
| XVIII | 100 |
| XXIV | 100 |
| Streptomycin | 0.2 |
| Isoniazid | 0.1 |
| Rifampycin | 0.05 |
| Ethambutol | 5.0 |
| Ofloxacin | 0.5 |

The data shown in Table 6 indicate that the tested compounds possess antimicrobial activity in respect to the used strain of M. tuberculosis in concentrations of 100 mg/l.

The other claimed compounds demonstrated lower activity.

Experiment 5. Determination of Psychodepressant Activity of the Claimed Compounds.

10 parameters that demonstrate possible development of behavioral depression were estimated in experiments on mice. Each parameter scores 2 points for an each mouse that had unchanged behavior. The total point sum was 60 (2×10×3 mice). Reducing score to less than 40 one hour after dosing with a substance per oral (300 mg/kg) denoted significant behavioral depression. Haloperidol was utilized as a reference agent.

TABLE 7

Psychodepressant action of the claimed substances.

| Substance | Point number |
| --- | --- |
| XII | 35 |
| Haloperidol | 27 |

The other claimed compounds were not tested for psychodepressant action.

Experiment 6. Evaluation of Analgesic Activity of the Claimed Compounds.

The time needed to draw back a tail placed under a directed source of radiant heat was estimated in a group of 3 mice. Prolongation of the response time by more than 50% after intraperitoneal dosing the substance (30 mg/kg) indicated analgesic activity. Analginum (2 mg/kg) was utilized as a reference agent.

TABLE 8

Evaluation of analgesic action of the claimed compounds.

| Preparation | Prolongation of the latent period of response (%) |
| --- | --- |
| XII | 96 |
| Analginum | 86 |

The other claimed compounds were not tested for analgesic action.

Experiment 7. Determination of Hepatoprotective Activity of the Claimed Compounds $CCl_4$ dissolved in 50% olive oil (1 ml/kg) was subcutaneously administrated to rats. Test substances were administrated perorally in a dose of 20 mg/kg 30 minutes before and 7 hours after the $CCl_4$ administration. The activity of alanine-aminotranspherase (AlAT), which is a marker enzyme of liver parenchyma damage, was assessed twenty-four hours later. Reducing of enzyme amount by more than 30% relative to the control group was considered as evidence of hepatoprotective properties of the substance. Vitamin E in a dose of 100 mg/kg was used as a reference agent.

TABLE 9

Assessment of hepatoprotective activity of the claimed substances

| Group | % of reducing AIAT |
|---|---|
| Intact | — |
| CCl$_4$ | — |
| XII | −48 |
| Vitamin E | −30 |

The other claimed compounds were not tested for hepatoprotective activity.

Experiment 8. Determination of Maximal Tolerable Dose

Tested substance was introduced orally (in dose of 300 mg/kg) through a gastric tube or intraperitoneally (in dose of 100 mg/kg) to no-breed white mice with mass 18–20 g (each tested group consisted of 3 males and 3 females). Then the mouse state was observed during 72 hours. Absence of symptoms characteristic of toxic effects, or absence of animal death during the given time allows to make a conclusion that the toxicity of the tested substance is low. If acute toxicity effects are observed, the dose is reduced to find maximal tolerable dose [4].

TABLE 9

Maximal tolerable dose

| NN | Compound | Concentration of tested compounds (mg/l) at oral introducing |
|---|---|---|
| 1 | Tween 80 | 300* |
| 2 | IV | 300 |
| 3 | VIII | 300 |
| 4 | XI | 300 |
| 5 | XII | 300 |
| 6 | XIII | 300 |
| 7 | XV | 300 |
| 8 | XVIII | 300 |
| 9 | XIX | 300 |
| 10 | XXIV | 300 |
| 11 | XXV | 300 |

*In all the cases including control the concentration of 300 mg/l was the maximally utilized concentration.

The obtained results show that the claimed compounds given by oral administration in the dose of 300 mg/l do not possess an acute toxicity on mice.

The other claimed compounds were not tested for toxicity.

INDUSTRIAL APPLICABILITY

The examples given above and practical results of synthesis and analysis of the claimed substances confirm possibility of laboratory and industrial synthesis of the claimed substances by the means that have been leant by modern pharmaceutical industry, and also their clear identification by commonly used control methods.

Series of experiments on determination of biological activity have shown, that the claimed compounds possess pronounced biological activity against various microorganisms, including antiviral activity against Herpes Simplex virus, interferon-inducing activity, antichlamydial activity, and also antimicrobial, psychodepressant, analgesic and hepatoprotective actions.

The presented data prove that the objectives stated by the invention have been achieved: new chemical compounds were synthesized, and these compounds possess low toxicity and extremely wide range of biological action.

Therefore, to our opinion, the claimed substances satisfy all the demands that are imposed upon an invention: they are new, not obvious, and industrially applicable.

Literature

1. Chatis P. A., Crumpacker C. S. Resistance of herpesviruses to antiviral drugs. Antimicrob. Agents Chemother. 1992; 36: 1589–1595.
2. Pharmaceutical microbiology. Ed. by W. B. Hugo and A. D. Russel. Blackwell Scientific Publications, Oxford, 1987, 511 p.
3. Esteban M., Paez E. Antiviral and antiproliferative properties of interferons: mechanism of action. Prog. med. virol. 1985, 32:159–173.
4. Irwin S., Psychopharmacology, 1968, 13, P. 222–257.
5. Gentry G. A., Lawrency N., Lushbaugh N. Isolation and differentiation of Herpes simplex virus and Trichomonas vaginalis in cell culture, J. of Clinical Microbiology 1985, Vol. 22, No. 2, P. 199–204.
6. Wang S-P., Grayston J. T. Serotyping of Chlamydia trachomatis by indirect fluorescent-antibody staining of inclusions in cell culture with monoclonal antibodies. J. of Clinical Microbiology, 1991, Vol.29, No. 7, P.1295–1298.
7. Judson B. A., Lambert P. P. Improved Syva MicroTrac Chlamydia trachomatis direct test method, Journal of Clinical Microbiology, 1988, Vol.26, No. 12, P.2657–2658.
8. Grosset J., Current problems with tuberculosis treatment, Res. Microbiology. 1996, Vol. 147, No. 10–16.
9. Goldner, Dietz, Carstens//Ann. Chem., 1966, No 691, p. 142; Ann. Chem., 1966, No 698, p.145, Ann. Chem., 1966, No 699, p. 145
10. Mashkovsky M. D. <<Drug means>> (in 2 parts, in Russian). Moscow, <<Medicine)>>, 1993, part 1, p.520-PROTOTYPE.

We claim:

1. A 2,4-dioxo-5-arylidenimino-1,3-pyrimidine of the formula:

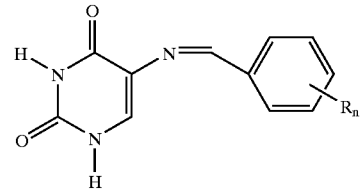

where n=1–3 and R is selected from the group consisting of hydroxyl, halogen, nitro, dialkylamino, dibenzo, and 3,4-dioxolano, with proviso that R is not hydroxyl and chloro at the same time, in any one molecule.

2. A compound of claim 1, wherein R is 4-Cl.
3. A compound of claim 1, wherein R is 3-Cl.
4. A compound of claim 1, wherein R is 2-Cl.
5. A compound of claim 1, wherein R is 4-Br.
6. A compound of claim 1, wherein R is 4-OH.
7. A compound of claim 1, wherein R is 2-OH-5-Br.
8. A compound of claim 1, wherein R is 2-OH-5-Br.
9. A compound of claim 1, wherein R is 4-F.
10. A compound of claim 1, wherein R is 2,4-Cl$_2$.
11. A compound of claim 1, wherein R is 2-OH-3,5-Br$_2$.
12. A compound of claim 1, wherein R is 4-NO$_2$.
13. A compound of claim 1, wherein R is 3-NO$_2$.
14. A compound of claim 1, wherein R is 2-NO$_2$.
15. A compound of claim 1, wherein R is 2-OH-5-NO$_2$.

16. A compound of claim 1, wherein R is 3,4-dioxolano.

17. A compound of claim 1, wherein R is 2-$NO_2$-4,5 dioxolano.

18. A compound of claim 1, wherein R is 2,3,5,6-dibenzo.

19. A compound of claim 1, wherein R is 2-OH-3,5-$I_2$.

20. A compound of claim 1, wherein R is 4-$N(CH_3)_2$.

* * * * *